(12) United States Patent
Silva et al.

(10) Patent No.: US 7,902,407 B2
(45) Date of Patent: *Mar. 8, 2011

(54) METHOD FOR PREPARATION OF SALTS OF HYDROXY-SUBSTITUTED AROMATIC COMPOUNDS

(75) Inventors: James Manio Silva, Clifton Park, NY (US); Thomas Link Guggenheim, Mt. Vernon, IN (US); David Winfield Woodruff, Saratoga Springs, NY (US)

(73) Assignee: Sabic Innovative Plastics IP B.V. (NL)

( * ) Notice: Subject to any disclaimer, the term of this patent is extended or adjusted under 35 U.S.C. 154(b) by 1386 days.

This patent is subject to a terminal disclaimer.

(21) Appl. No.: 11/095,200

(22) Filed: Mar. 30, 2005

(65) Prior Publication Data

US 2006/0224024 A1    Oct. 5, 2006

(51) Int. Cl.
C07C 39/12 (2006.01)
C07C 39/16 (2006.01)

(52) U.S. Cl. .......................... 568/716; 568/723

(58) Field of Classification Search .................. 568/716, 568/723
See application file for complete search history.

(56) References Cited

U.S. PATENT DOCUMENTS

| 3,847,869 | A |  | 11/1974 | Williams |
| 3,879,428 | A |  | 4/1975 | Heath et al. |
| 4,202,993 | A |  | 5/1980 | Takekoshi |
| 4,243,822 | A |  | 1/1981 | Demler et al. |
| 4,257,953 | A |  | 3/1981 | Williams et al. |
| 4,302,616 | A |  | 11/1981 | Williams et al. |
| 4,492,806 | A | * | 1/1985 | Mendiratta et al. ........... 568/723 |
| 4,546,207 | A |  | 10/1985 | Mendiratta et al. |
| 5,851,837 | A |  | 12/1998 | Stokes et al. |
| 7,115,785 | B2 | * | 10/2006 | Guggenheim et al. ........ 568/723 |

OTHER PUBLICATIONS

U.S. Appl. No. 10/647,890, filed Aug. 25, 2003, entitled "*Method for Making Salts of Hydroxy-Substituted Hydrocarbons*".

* cited by examiner

*Primary Examiner* — Sikarl A Witherspoon
(74) *Attorney, Agent, or Firm* — Cantor Colburn LLP

(57) ABSTRACT

A method for preparing a metal salt of a hydroxy-substituted aromatic compound is described. The method comprises contacting in an aqueous medium at least one hydroxy-substituted aromatic compound with a base comprising a metal cation to provide a mixture comprising water and a metal salt of said hydroxy-substituted aromatic compound. The aqueous metal salt is then contacted with a substantially water-immiscible solvent at a temperature greater than the boiling point of water at the prevailing pressure to provide a slurry comprising the metal salt of the hydroxy-substituted aromatic compound and a vapor stream comprising the water-immiscible solvent and water. The components of the vapor stream are separated using a vapor handling system comprising a partial reflux condenser to provide a water-rich component and a water immiscible solvent-rich component.

20 Claims, No Drawings

METHOD FOR PREPARATION OF SALTS OF HYDROXY-SUBSTITUTED AROMATIC COMPOUNDS

BACKGROUND OF INVENTION

This invention relates to a method for making salts of hydroxy-substituted aromatic compounds. In one particular embodiment the invention relates to the preparation of alkali metal salts of hydroxy-substituted aromatic compounds.

Salts of hydroxy-substituted aromatic compounds find varied uses in the industry. They are frequently required for synthesis of hydroxy-substituted aromatic derivatives or for use as bases in chemical reactions. Various methods are known in the art for the preparation of salts of hydroxy-substituted aromatic compounds, more important among those being the methods of forming the dry salt.

U.S. Pat. No. 4,520,204 describes the manufacture of salts such as bisphenol A disodium salt by forming the salt in an aqueous solution with sodium hydroxide and adding the aqueous solution to boiling ortho-dichlorobenzene (oDCB) to dry the salt by azeotropically distilling water. The salt slurry in organic solvent is further dried by refluxing over calcium hydride. The distillate is refluxed over $CaH_2$ and returned to the reaction vessel. The procedure is problematic in that foaming may occur during the addition of the aqueous salt solution to the refluxing ortho-dichlorobenzene. Further, this process requires careful attention in order to maintain the inventory of boiling oDCB during introduction of the aqueous solution.

U.S. Pat. No. 4,546,207 describes the manufacture of anhydrous salts of dihydroxy aromatic compounds by forming the salt in an aqueous solution with excess sodium hydroxide and then isolating the solid salt from the reaction mixture. The solid salt is then treated with an organic solvent and the mixture evaporated to dry the salt. With this procedure, the salt may be contaminated with excess sodium hydroxide, which interferes with subsequent reactions.

U.S. Pat. No. 4,257,953 describes a process for bisphenoxide salt preparation in which a bisphenoxide salt, e.g. aqueous bisphenol A disodium salt, is mixed with a solvent, e.g. toluene, and the water is removed by azeotropic distillation. However this process results in substantial accumulation of solid salt on the vessel walls.

U.S. Pat. No. 4,492,806 describes a process for bisphenol metal salt preparation and drying in which a solvent mixture comprising an aliphatic alcohol and a solvent such as toluene are mixed with an aqueous bisphenol metal salt solution, and the volatile species (alcohol and water) are azeotropically removed, yielding a dry fine slurry of bisphenol metal salt. Though this method is effective for bisphenol A disodium salt preparation, it requires an alcohol co-solvent, which introduces process complexity and also a flammable solvent.

Hence, there exists a need to provide alternate methods for preparing dry metal salts of hydroxy-substituted aromatic compounds.

BRIEF SUMMARY OF THE INVENTION

In one embodiment the present invention provides a method for preparing a metal salt of a hydroxy-substituted aromatic compound, said method comprising steps (a)-(d):

(a) contacting in an aqueous medium at least one hydroxy-substituted aromatic compound with a base comprising a metal cation to provide a mixture comprising water and a metal salt of said hydroxy-substituted aromatic compound;

(b) contacting the mixture formed in step (a) with a substantially water-immiscible solvent at a temperature greater than the boiling point of water at the prevailing pressure to provide a slurry comprising the metal salt of the hydroxy-substituted aromatic compound and the water-immiscible solvent, and a vapor stream comprising the water-immiscible solvent and water;

(c) introducing the vapor stream into a vapor handling system comprising a partial reflux condenser; and (d) separating the vapor stream to provide a water-rich component and a water immiscible solvent-rich component.

In another embodiment the present invention provides a method for preparing an alkali metal salt of a hydroxy-substituted aromatic compound of formula IV, said method comprising steps (a)-(d):

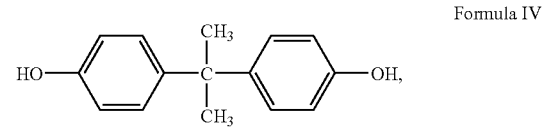

Formula IV (a) contacting in an aqueous medium the hydroxy-substituted aromatic compound of formula IV with a base comprising an alkali metal cation to provide a mixture comprising water and an alkali metal salt of said hydroxy-substituted aromatic compound of formula IV;

(b) contacting the mixture formed in step (a) with a substantially water-immiscible solvent at a temperature greater than the boiling point of water at the prevailing pressure to provide a slurry comprising the alkali metal salt of the hydroxy-substituted aromatic compound of formula IV and the water-immiscible solvent, and a vapor stream comprising the substantially water-immiscible solvent and water;

(c) introducing the vapor stream into a vapor handling system comprising a partial reflux condenser; and (d) separating the vapor stream to provide a water-rich component and a water immiscible solvent-rich component.

In another embodiment the present invention provides a method for preparing an alkali metal salt of a hydroxy-substituted aromatic compound of formula V, said method comprising steps (a)-(d):

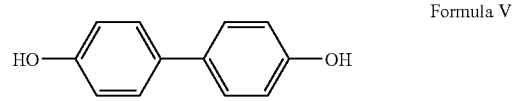

Formula V (a) contacting in an aqueous medium the hydroxy-substituted aromatic compound of formula V with a base comprising an alkali metal cation to provide a mixture comprising water and an alkali metal salt of said hydroxy-substituted aromatic compound of formula V;

(b) contacting the mixture formed in step (a) with a substantially water-immiscible solvent at a temperature greater than the boiling point of water at the prevailing pressure to provide a slurry comprising the alkali metal salt of the hydroxy-substituted aromatic compound of formula V and the water-immiscible solvent, and a vapor stream comprising the substantially water-immiscible solvent and water;

(c) introducing the vapor stream into a vapor handling system comprising a partial reflux condenser; and (d) separating the vapor stream to provide a water-rich component and a water immiscible solvent-rich component.

DETAILED DESCRIPTION OF THE INVENTION

The present invention may be understood more readily by reference to the following detailed description of preferred embodiments of the invention and the examples included therein. In the following specification and the claims which follow, reference will be made to a number of terms which shall be defined to have the following meanings:

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

The modifier "about" used in connection with a quantity is inclusive of the stated value and has the meaning dictated by the context (e.g., includes the degree of error associated with measurement of the particular quantity).

As used herein the term "aliphatic radical" refers to a radical having a valence of at least one consisting of a linear or branched array of atoms that is not cyclic. The array may include heteroatoms such as nitrogen, sulfur, silicon, selenium and oxygen or may be composed exclusively of carbon and hydrogen. Aliphatic radicals may be "substituted" or "unsubstituted". A substituted aliphatic radical is defined as an aliphatic radical which comprises at least one substituent. A substituted aliphatic radical may comprise as many substituents as there are positions available on the aliphatic radical for substitution. Substituents which may be present on an aliphatic radical include but are not limited to halogen atoms such as fluorine, chlorine, bromine, and iodine. Substituted aliphatic radicals include trifluoromethyl; hexafluoroisopropylidene; chloromethyl; difluorovinylidene; trichloromethyl, bromoethyl, bromotrimethylene (e.g. —$CH_2CHBrCH_2$—), and the like. For convenience, the term "unsubstituted aliphatic radical" is defined herein to encompass, as part of the "linear or branched array of atoms which is not cyclic" comprising the unsubstituted aliphatic radical, a wide range of functional groups. Examples of unsubstituted aliphatic radicals include allyl, aminocarbonyl (i.e. —$CONH_2$), carbonyl, dicyanoisopropylidene (i.e. —$CH_2C(CN)_2CH_2$—), methyl (i.e. —$CH_3$), methylene (i.e. —$CH_2$—), ethyl, ethylene, formyl, hexyl, hexamethylene, hydroxymethyl (i.e. —$CH_2OH$), mercaptomethyl (i.e. —$CH_2SH$), methylthio (i.e. —$SCH_3$), methylthiomethyl (i.e. —$CH_2SCH_3$), methoxy, methoxycarbonyl, nitromethyl (i.e. —$CH_2NO_2$), thiocarbonyl, trimethylsilyl, t-butyldimethylsilyl, trimethyoxysilylpropyl, vinyl, vinylidene, and the like. Aliphatic radicals are defined to comprise at least one carbon atom. A $C_1$-$C_{10}$ aliphatic radical includes substituted aliphatic radicals and unsubstituted aliphatic radicals containing at least one but no more than 10 carbon atoms.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthracenyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. Aromatic radicals may be "substituted" or "unsubstituted". A substituted aromatic radical is defined as an aromatic radical which comprises at least one substituent. A substituted aromatic radical may comprise as many substituents as there are positions available on the aromatic radical for substitution. Substituents which may be present on an aromatic radical include, but are not limited to halogen atoms such as fluorine, chlorine, bromine, and iodine. Substituted aromatic radicals include trifluoromethylphenyl, hexafluoroisopropylidenebis(4-phenyloxy) (i.e. —$OPhC(CF_3)_2PhO$—), chloromethylphenyl; 3-trifluorovinyl-2-thienyl; 3-trichloromethylphenyl (i.e. 3-$CCl_3Ph$-), bromopropylphenyl (i.e. $BrCH_2CH_2CH_2Ph$-), and the like. For convenience, the term "unsubstituted aromatic radical" is defined herein to encompass, as part of the "array of atoms having a valence of at least one comprising at least one aromatic group", a wide range of functional groups. Examples of unsubstituted aromatic radicals include 4-allyloxyphenoxy, aminophenyl (i.e. $H_2NPh$-), aminocarbonylphenyl (i.e. $NH_2COPh$-), 4-benzoylphenyl, dicyanoisopropylidenebis(4-phenyloxy) (i.e. —$OPhC(CN)_2PhO$—), 3-methylphenyl, methylenebis(4-phenyloxy) (i.e. —$OPhCH_2PhO$—), ethylphenyl, phenylethenyl, 3-formyl-2-thienyl, 2-hexyl-5-furanyl; hexamethylene-1,6-bis(4-phenyloxy) (i.e. —$OPh(CH_2)_6PhO$—); 4-hydroxymethylphenyl (i.e. 4-$HOCH_2Ph$-), 4-mercaptomethylphenyl (i.e. 4-$HSCH_2Ph$-), 4-methylthiophenyl (i.e. 4-$CH_3SPh$-), methoxyphenyl, methoxycarbonylphenyloxy (e.g. methyl salicyl), nitromethylphenyl (i.e. -$PhCH_2NO_2$), trimethylsilylphenyl, t-butyldimethylsilylphenyl, vinylphenyl, vinylidenebis(phenyl), and the like. The term "a $C_3$-$C_{10}$ aromatic radical" includes substituted aromatic radicals and unsubstituted aromatic radicals containing at least three but no more than 10 carbon atoms. The aromatic radical 1-imidazolyl ($C_3H_2N_2$—) represents a $C_3$ aromatic radical. The benzyl radical ($C_7H_8$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. Cycloaliphatic radicals may be "substituted" or "unsubstituted". A substituted cycloaliphatic radical is defined as a cycloaliphatic radical which comprises at least one substituent. A substituted cycloaliphatic radical may comprise as many substituents as there are positions available on the cycloaliphatic radical for substitution. Substituents which may be present on a cycloaliphatic radical include but are not limited to halogen atoms such as fluorine, chlorine, bromine, and iodine. Substituted cycloaliphatic radicals include trifluoromethylcyclohexyl, hexafluoroisopropylidenebis(4-cyclohexyloxy) (i.e. —$OC_6H_{10}C(CF_3)_2C_6H_{10}O$—), chloromethylcyclohexyl; 3-trifluorovinyl-2-cyclopropyl; 3-trichloromethylcyclohexyl (i.e. 3-$CCl_3C_6H_{10}$—), bromopropylcyclohexyl (i.e.

BrCH$_2$CH$_2$CH$_2$C$_6$H$_{10}$—), and the like. For convenience, the term "unsubstituted cycloaliphatic radical" is defined herein to encompass a wide range of functional groups. Examples of cycloaliphatic radicals include 4-allyloxycyclohexyl, aminocyclohexyl (i.e. H$_2$NC$_6$H$_{10}$—), aminocarbonylcyclopentyl (i.e. NH$_2$COC$_5$H$_8$—), 4-acetyloxycyclohexyl, dicyanoisopropylidenebis(4-cyclohexyloxy) (i.e. —O C$_6$H$_{10}$C(CN)$_2$ C$_6$H$_{10}$O—), 3-methylcyclohexyl, methylenebis(4-cyclohexyloxy) (i.e. —OC$_6$H$_{10}$CH$_2$C$_6$H$_{10}$O—), ethylcyclobutyl, cyclopropylethenyl, 3-formyl-2-terahydrofuranyl, 2-hexyl-5-tetrahydrofuranyl; hexamethylene-1,6-bis(4-cyclohexyloxy) (i.e. —OC$_6$H$_{10}$(CH$_2$)$_6$C$_6$H$_{10}$O—); 4-hydroxymethylcyclohexyl (i.e. 4-HOCH$_2$C$_6$H$_{10}$—), 4-mercaptomethylcyclohexyl (i.e. 4-HSCH$_2$C$_6$H$_{10}$—), 4-methylthiocyclohexyl (i.e. 4-CH$_3$SC$_6$H$_{10}$—), 4-methoxycyclohexyl, 2-methoxycarbonylcyclohexyloxy (2-CH$_3$OCO C$_6$H$_{10}$O—), nitromethylcyclohexyl (i.e. NO$_2$CH$_2$C$_6$H$_{10}$—), trimethylsilylcyclohexyl, t-butyldimethylsilylcyclopentyl, 4-trimethoxysilylethylcyclohexyl (e.g. (CH$_3$O)$_3$ SiCH$_2$CH$_2$C$_6$H$_{10}$—), vinylcyclohexenyl, vinylidenebis(cyclohexyl), and the like. The term "a C$_3$-C$_{10}$ cycloaliphatic radical" includes substituted cycloaliphatic radicals and unsubstituted cycloaliphatic radicals containing at least three but no more than 10 carbon atoms. The cycloaliphatic radical 2-tetrahydrofuranyl (C$_4$H$_7$O—) represents a C$_4$ cycloaliphatic radical. The cyclohexylmethyl radical (C$_6$H$_{11}$CH$_2$—) represents a C$_7$ cycloaliphatic radical.

As noted the present invention generally refers to a method for preparing a metal salt of a hydroxy-substituted aromatic compound. It has been discovered that the method of the present invention provides a dry metal salt of hydroxy-substituted aromatic compound, wherein the dry salt has a suitable particle size distribution. It has been discovered that, employing a partial reflux condenser on the sprayover vessel during step "b" of the process of this invention facilitates sprayover by minimizing or eliminating solvent inventory control problems and further enables sprayover at higher temperatures, which is essential both to achieve a suitable particle size distribution and to avoid caking on vessel walls for some hydroxy-substituted aromatic compounds.

In one embodiment the method for preparing a metal salt of a hydroxy-substituted aromatic compound according to the present invention comprises steps (a)-(d):

(a) contacting in an aqueous medium at least one hydroxy-substituted aromatic compound with a base comprising a metal cation to provide a mixture comprising water and a metal salt of said hydroxy-substituted aromatic compound;

(b) contacting the mixture formed in step (a) with a substantially water-immiscible solvent at a temperature greater than the boiling point of water at the prevailing pressure to provide a slurry comprising the metal salt of the hydroxy-substituted aromatic compound and the water immiscible solvent, and a vapor stream comprising the substantially water-immiscible solvent and water;

(c) introducing the vapor stream into a vapor handling system comprising a partial reflux condenser; and (d) separating the vapor stream to provide a water-rich component and a water immiscible solvent-rich component.

In another embodiment of the present invention, a solution of a metal salt of hydroxy-substituted aromatic compound in water and optionally a water-miscible co-solvent is introduced into a vessel containing a water-immiscible solvent that is maintained at a temperature above a predetermined minimum temperature and below the boiling point of the water-immiscible solvent at the prevailing pressure, said vessel being equipped with a partial reflux condenser that is cooled such that the reflux temperature is above the boiling point of water at the prevailing pressure. This step yields a slurry of the metal salt in the water-immiscible solvent and a vapor stream comprising the water-immiscible solvent, water, and, optionally the co-solvent. This step is sometimes referred to as "sprayover". The slurry of the product salt of hydroxy-substituted aromatic compound may be further dried by distilling additional water-immiscible solvent and moisture out of the vessel.

In one embodiment the hydroxy-substituted aromatic compound is selected from the group consisting of monohydroxy-substituted aromatic compounds; dihydroxy-substituted aromatic compounds; trihydroxy-substituted aromatic compounds; tetrahydroxy-substituted aromatic compounds and mixtures thereof. As used herein the term "mixtures thereof" is defined as combinations of two or more hydroxy-substituted aromatic compounds described above. Monohydroxy-substituted aromatic compounds are illustrated by phenol, p-cresol, p-cumylphenol, and the like. Dihydroxy-substituted aromatic compounds are illustrated by dihydroxybenzenes such as hydroquinone, resorcinol, and the like. Dihydroxy-substituted aromatic compounds are further illustrated by bisphenols such as bisphenol A and biphenols such as 4,4'-dihydroxybiphenyl. Trihydroxy-substituted aromatic compounds are illustrated by 1,3-5-trihydroxybenzene; 1,1,1-tris(4-hydroxyphenyl)ethane (THPE); and the like. Tetrahydroxy-substituted aromatic compounds are illustrated by 2,2-bis(3,4-dihydroxyphenyl)propane; 3,4,3',4'-tetrahydroxybiphenyl; and the like.

Suitable hydroxy-substituted aromatic compounds include at least one dihydroxy-substituted aromatic compound having formula I

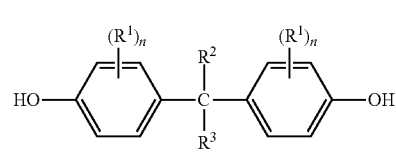

Formula I wherein $R^1$ is independently at each occurrence a halogen, a $C_1$-$C_{30}$ aliphatic radical, a $C_3$-$C_{30}$ cycloaliphatic radical, or a $C_3$-$C_{30}$ aromatic radical, $R^2$ and $R^3$ are independently hydrogen, a $C_1$-$C_{30}$ aliphatic radical, a $C_3$-$C_{30}$ cycloaliphatic radical, or a $C_3$-$C_{30}$ aromatic radical or $R^2$ and $R^3$ together form a $C_3$-$C_{20}$ cycloaliphatic radical and "n" is independently at each occurrence an integer having a value 0 to 4.

The hydroxy-substituted aromatic compounds having a formula I are illustrated by bisphenols selected from the group consisting of 1,1-bis(4-hydroxyphenyl)cyclopentane; 2,2-bis(3-allyl-4-hydroxyphenyl)propane; 2,2-bis(2-t-butyl-4-hydroxy-5-methylphenyl)propane; 2,2-bis(3-t-butyl-4-hydroxy-6-methylphenyl)propane; 2,2-bis(3-t-butyl-4-hydroxy-6-methylphenyl)butane; 2,2-bis(3-methyl-4-hydroxyphenyl)propane; 2,2-bis(4-hydroxyphenyl)-1,1,1,3,3,3-hexafluoropropane; 1,1-bis(4-hydroxyphenyl)-2,2,2-trichloroethane; 1,1-bis(4-hydroxyphenyl)norbornane; 1,2-bis(4-hydroxyphenyl)ethane; 1,3-bis(4-hydroxyphenyl) propenone; bis(4-hydroxyphenyl) sulfide; 4,4-bis(4-hydroxyphenyl)pentanoic acid; 4,4-bis(3,5-dimethyl-4-hydroxyphenyl)pentanoic acid; 2,2-bis(4-hydroxyphenyl) acetic acid; 2,4'-dihydroxydiphenylmethane; bis(2-hydroxyphenyl)methane; bis(4-hydroxyphenyl)methane; bis (4-hydroxy-5-nitrophenyl)methane; bis(4-hydroxy-2,6-dimethyl-3-methoxyphenyl)methane; 1,1-bis(4-hydroxyphenyl)ethane; 1,1-bis(4-hydroxy-2-chlorophenyl)

ethane; 2,2-bis(4-hydroxyphenyl)propane (bisphenol-A); 1,1-bis(4-hydroxyphenyl)propane; 2,2-bis(3-chloro-4-hydroxyphenyl)propane; 2,2-bis(3-bromo-4-hydroxyphenyl)propane; 2,2-bis(4-hydroxy-3-methylphenyl)propane; 2,2-bis(4-hydroxy-3-isopropylphenyl)propane; 2,2-bis(3-t-butyl-4-hydroxyphenyl)propane; 2,2-bis(3-phenyl-4-hydroxyphenyl)propane; 2,2-bis(3,5-dichloro-4-hydroxyphenyl)propane; 2,2-bis(3,5-dibromo-4-hydroxyphenyl)propane; 2,2-bis(3,5-dimethyl-4-hydroxyphenyl)propane; 2,2-bis(3-chloro-4-hydroxy-5-methylphenyl)propane; 2,2-bis(3-bromo-4-hydroxy-5-methylphenyl)propane; 2,2-bis(3-chloro-4-hydroxy-5-isopropylphenyl)propane; 2,2-bis(3-bromo-4-hydroxy-5-isopropylphenyl)propane; 2,2-bis(3-t-butyl-5-chloro-4-hydroxyphenyl)propane; 2,2-bis(3-bromo-5-t-butyl-4-hydroxyphenyl)propane; 2,2-bis(3-chloro-5-phenyl-4-hydroxyphenyl)propane; 2,2-bis(3-bromo-5-phenyl-4-hydroxyphenyl)propane; 2,2-bis(3,5-disopropyl-4-hydroxyphenyl)propane; 2,2-bis(3,5-di-t-butyl-4-hydroxyphenyl)propane; 2,2-bis(3,5-diphenyl-4-hydroxyphenyl)propane; 2,2-bis(4-hydroxy-2,3,5,6-tetrachlorophenyl)propane; 2,2-bis(4-hydroxy-2,3,5,6-tetrabromophenyl)propane; 2,2-bis(4-hydroxy-2,3,5,6-tetramethylphenyl)propane; 2,2-bis(2,6-dichloro-3,5-dimethyl-4-hydroxyphenyl)propane; 2,2-bis(2,6-dibromo-3,5-dimethyl-4-hydroxyphenyl)propane; 2,2-bis(4-hydroxy-3-ethylphenyl)propane; 2,2-bis(4-hydroxy-3,5-dimethylphenyl)propane; 2,2-bis(3,5,3',5'-tetrachloro-4,4'-dihydroxyphenyl)propane; 1,1-bis(4-hydroxyphenyl)cyclohexylmethane; 2,2-bis(4-hydroxyphenyl)-1-phenylpropane; 1,1-bis(4-hydroxyphenyl)cyclohexane; 1,1-bis(3-chloro-4-hydroxyphenyl)cyclohexane; 1,1-bis(3-bromo-4-hydroxyphenyl)cyclohexane; 1,1-bis(4-hydroxy-3-methylphenyl)cyclohexane; 1,1-bis(4-hydroxy-3-isopropylphenyl)cyclohexane; 1,1-bis(3-t-butyl-4-hydroxyphenyl)cyclohexane; 1,1-bis(3-phenyl-4-hydroxyphenyl)cyclohexane; 1,1-bis(3,5-dichloro-4-hydroxyphenyl)cyclohexane; 1,1-bis(3,5-dibromo-4-hydroxyphenyl)cyclohexane; 1,1-bis(3,5-dimethyl-4-hydroxyphenyl)cyclohexane; 1,1-bis(3-chloro-4-hydroxy-5-methylphenyl)cyclohexane; 1,1-bis(3-bromo-4-hydroxy-5-methylphenyl)cyclohexane; 1,1-bis(3-chloro-4-hydroxy-5-isopropylphenyl)cyclohexane; 1,1-bis(3-bromo-4-hydroxy-5-isopropylphenyl)cyclohexane; 1,1-bis(3-t-butyl-5-chloro-4-hydroxyphenyl)cyclohexane; 1,1-bis(3-bromo-5-t-butyl-4-hydroxyphenyl)cyclohexane; 1,1-bis(3-chloro-5-phenyl-4-hydroxyphenyl)cyclohexane; 1,1-bis(3-bromo-5-phenyl-4-hydroxyphenyl)cyclohexane; 1,1-bis(3,5-disopropyl-4-hydroxyphenyl)cyclohexane; 1,1-bis(3,5-di-t-butyl-4-hydroxyphenyl)cyclohexane; 1,1-bis(3,5-diphenyl-4-hydroxyphenyl)cyclohexane; 1,1-bis(4-hydroxy-2,3,5,6-tetrachlorophenyl)cyclohexane; 1,1-bis(4-hydroxy-2,3,5,6-tetrabromophenyl)cyclohexane; 1,1-bis(4-hydroxy-2,3,5,6-tetramethylphenyl)cyclohexane; 1,1-bis(2,6-dichloro-3,5-dimethyl-4-hydroxyphenyl)cyclohexane; 1,1-bis(2,6-dibromo-3,5-dimethyl-4-hydroxyphenyl)cyclohexane; 1,1-bis(4-hydroxyphenyl)-3,3,5-trimethylcyclohexane; 1,1-bis(3-chloro-4-hydroxyphenyl)-3,3,5-trimethylcyclohexane; 1,1-bis(3-bromo-4-hydroxyphenyl)-3,3,5-trimethylcyclohexane; 1,1-bis(4-hydroxy-3-methylphenyl)-3,3,5-trimethylcyclohexane; 1,1-bis(4-hydroxy-3-isopropylphenyl)-3,3,5-trimethylcyclohexane; 1,1-bis(3-t-butyl-4-hydroxyphenyl)-3,3,5-trimethylcyclohexane; 1,1-bis(3-phenyl-4-hydroxyphenyl)-3,3,5-trimethylcyclohexane; 1,1-bis(3,5-dichloro-4-hydroxyphenyl)-3,3,5-trimethylcyclohexane; 1,1-bis(3,5-dibromo-4-hydroxyphenyl)-3,3,5-trimethylcyclohexane; 1,1-bis(3,5-dimethyl-4-hydroxyphenyl)-3,3,5-trimethylcyclohexane; 1,1-bis(3-chloro-4-hydroxy-5-methylphenyl)-3,3,5-trimethylcyclohexane; 1,1-bis(3-bromo-4-hydroxy-5-methylphenyl)-3,3,5-trimethylcyclohexane; 1,1-bis(3-chloro-4-hydroxy-5-isopropylphenyl)-3,3,5-trimethylcyclohexane; 1,1-bis(3-bromo-4-hydroxy-5-isopropylphenyl)-3,3,5-trimethylcyclohexane; 1,1-bis(3-t-butyl-5-chloro-4-hydroxyphenyl)-3,3,5-trimethylcyclohexane; 1,1-bis(3-bromo-5-t-butyl-4-hydroxyphenyl)-3,3,5-trimethylcyclohexane; bis(3-chloro-5-phenyl-4-hydroxyphenyl)-3,3,5-trimethylcyclohexane; 1,1-bis(3-bromo-5-phenyl-4-hydroxyphenyl)-3,3,5-trimethylcyclohexane; 1,1-bis(3,5-disopropyl-4-hydroxyphenyl)-3,3,5-trimethylcyclohexane; 1,1-bis(3,5-di-t-butyl-4-hydroxyphenyl)-3,3,5-trimethylcyclohexane; 1,1-bis(3,5-diphenyl-4-hydroxyphenyl)-3,3,5-trimethylcyclohexane; 1,1-bis(4-hydroxy-2,3,5,6-tetrachlorophenyl)-3,3,5-trimethylcyclohexane; 1,1-bis(4-hydroxy-2,3,5,6-tetrabromophenyl)-3,3,5-trimethylcyclohexane; 1,1-bis(4-hydroxy-2,3,5,6-tetramethylphenyl)-3,3,5-trimethylcyclohexane; 1,1-bis(2,6-dichloro-3,5-dimethyl-4-hydroxyphenyl)-3,3,5-trimethylcyclohexane; 1,1-bis(2,6-dibromo-3,5-dimethyl-4-hydroxyphenyl)-3,3,5-trimethylcyclohexane; 4,4-bis(4-hydroxyphenyl)heptane; 1,1-bis(4-hydroxyphenyl)decane; 1,1-bis(4-hydroxyphenyl)cyclododecane; 1,1-bis(3,5-dimethyl-4-hydroxyphenyl)cyclododecane; and bis(4-hydroxyphenyl)methane.

In one embodiment suitable hydroxy-substituted aromatic compound includes at least one dihydroxy-substituted aromatic compound having formula II

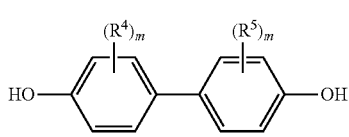

Formula II wherein $R^4$ and $R^5$ are independently at each occurrence halogen, a $C_1$-$C_{30}$ aliphatic radical, a $C_3$-$C_{30}$ cycloaliphatic radical, or a $C_3$-$C_{30}$ aromatic radical, and "m" is independently at each occurrence an integer having a value 0 to 4.

Suitable hydroxy-substituted aromatic compounds having formula II are illustrated by the group consisting of 4,4'-biphenol; 2,2',6,6'-tetramethyl-3,3',5,5'-tetrabromo-4,4'-biphenol; 2,2',6,6'-tetramethyl-3,3',5-tribromo-4,4'-biphenol; 4,4'-dihydroxy-3,3'-dimethyl-1,1-biphenyl; 4,4'-dihydroxy-3,3'-dioctyl-1,1-biphenyl; 3,3',5,5'-tetramethyl4,4'-biphenol.

In yet another embodiment suitable hydroxy-substituted aromatic compounds may be selected from compounds having formula IV (2,2-bis(4-hydroxyphenyl)propane (bisphenol-A)) and formula V (4,4'-dihydroxydiphenyl).

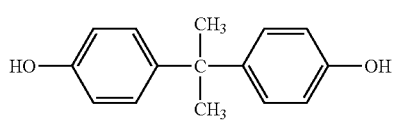

Formula IV

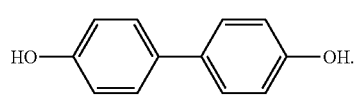

Formula V

The aqueous medium as described herein refers to a medium comprising water. Further the aqueous medium in the present context refers to a medium in which a hydroxy-substituted aromatic compound reacts to form a metal salt in the presence of a base comprising a metal cation. In one embodiment the aqueous medium is such that the hydroxy-substituted aromatic compound is at least partially soluble. In another embodiment the aqueous medium is such that a hydroxy-substituted aromatic compound is essentially completely soluble in the aqueous medium. In another embodiment the hydroxy-substituted aromatic compound is at least partially insoluble in the aqueous medium and is solubilized in the presence of a base comprising a metal cation, on the formation of the corresponding metal salt of the hydroxy-substituted aromatic compound.

In one embodiment the aqueous medium comprises water and, optionally, at least one substantially water-miscible organic solvent (hereinafter at times referred to as co-solvent). Substantially water-miscible in the present context refers to a solubility of the organic co-solvent in water of greater than about 90% or greater than about 95% or greater than about 98% or greater than about 99% by weight under the reactions conditions. Water-miscible organic solvents are well-known in the art and typically comprise hydroxy-substituted aliphatic compounds including, but not limited to, methanol, ethanol, propanol, butanol, ethylene glycol, propylene glycol, and mixtures of the foregoing water-miscible organic solvents. In one embodiment when the solvent medium comprises water and at least one substantially water-miscible organic solvent, then the amount of said water-miscible organic solvent may be in a range of between about 10 weight % and about 95 weight % based on the total weight of water and the water-miscible organic solvent. In another embodiment the amount ranges from about 60 weight % to about 95 weight %. In a yet another embodiment the amount of said water-miscible organic solvent may be in a range of between about 80 weight % and about 95 weight % based on the total weight of water and the water-miscible organic solvent. In some particular embodiments the amount of said water-miscible organic solvent is sufficient to essentially effect complete solubility of hydroxy-substituted aromatic compound in a mixture with water.

In one embodiment a metal salt of a hydroxy-substituted aromatic compound may be prepared by contacting at least one hydroxy-substituted aromatic compound and at least one base comprising a metal cation in an aqueous medium comprising water and, optionally, a water miscible organic solvent. The base comprising a metal cation includes a metal hydroxide selected from the group consisting of, but not limited to, alkali metal hydroxide and alkaline-earth metal hydroxide. In one embodiment an alkali metal hydroxide is employed as the base comprising a metal cation. In yet another embodiment the base used is sodium hydroxide.

The base may be employed in any convenient form. Typically, the base is employed as an aqueous solution. In an illustrative example an aqueous solution containing about 30-70% by weight of the base in water is suitable. Solutions comprising about 50% by weight concentration of the base are readily available and their use may be preferred. In another embodiment a solid base may be used. Illustrative, non-limiting examples of solid bases comprise solid alkali metal hydroxides such as sodium hydroxide and potassium hydroxide and solid alkaline-earth metal hydroxides like calcium hydroxide and magnesium hydroxide.

In various embodiments the contacting of the hydroxy-substituted aromatic compound with the base may be performed using stoichiometric amounts wherein the base and the hydroxy-substituted aromatic compound are present in amounts corresponding to a molar ratio of base to hydroxy-substituted aromatic compound which in one embodiment deviates from ideal stoichiometry by no more than 0.4 mole %. In another embodiment the molar ratio deviates from ideal stoichiometry by no more than 0.2 mole %. In yet another embodiment the molar ratio deviates from ideal stoichiometry by no more than 0.1 mole %.

The contacting of the hydroxy-substituted aromatic compound may be performed in the aqueous medium at a temperature which provides for the efficient conversion of the hydroxy-substituted aromatic compound to the corresponding metal salt. In one embodiment the temperature ranges from about 50° C. to 150° C. In another embodiment the temperature at which the metal salt is prepared ranges from about 70° C. to about 100° C. In yet another embodiment the temperature ranges from about 80° C. to about 100° C.

In one embodiment the contacting of the hydroxy-substituted aromatic compound with the base may be typically performed in the aqueous medium for a period of time sufficient to obtain the desired degree of conversion to the metal salt. In various embodiments the contact time depends upon a number of factors including, but not limited to, the amounts of hydroxy-substituted aromatic compound and the base employed. In a particular embodiment the contact time is for greater than about 1 hour. In one embodiment the contact time is for about 1.5 hours to 3 hours. Appropriate contact times depend upon reaction temperatures and the nature of the reactants, and this may be determined by one skilled in the art, without undue experimentation.

In one embodiment the contacting of the hydroxy-substituted aromatic compound with the base in an aqueous medium, may be performed under an inert atmosphere, such as under nitrogen, argon or helium.

In one embodiment the contacting of the hydroxy-substituted aromatic compound with the base in an aqueous medium, may be performed at a solids level of greater than about 5%, wherein the solids level is the weight of salt of the hydroxy-substituted aromatic compound divided by the sum of weight of the reactants and weight of the aqueous solvent. In another embodiment the solids level is greater than about 15%. In yet another embodiment the solids level is greater than about 25%. The course of the reaction may be monitored by known methods.

Once the salt is formed the mixture comprising the metal salt in the aqueous medium is maintained at a temperature, so as to maintain the metal salt of hydroxy-substituted aromatic compound in solution. The metal salt is then dried in two stages. The metal salt solution in the aqueous medium is at first contacted with a substantially water-immiscible solvent contained in a drying vessel. The substantially water-immiscible solvent contained in the drying vessel is maintained at a temperature which is greater than the boiling point of water at the prevailing pressure. On contacting the solution comprising the metal salt in the aqueous medium with a water-immiscible solvent, a slurry comprising the metal salt of the hydroxy-substituted aromatic compound and the water immiscible solvent, and a vapor stream comprising the substantially water-immiscible solvent and water and water-miscible organic co-solvent (if present) are obtained. Substantially water-immiscible solvent means that the solvent is soluble to the extent of less than about 10% by weight or less than about 5% by weight or less than about 1% by weight in water; or that water is soluble to the extent of less than about 10% by weight or less than about 5% by weight or less than about 1% by weight in the solvent.

In various embodiments the temperature at which the water-immiscible solvent is maintained ranges from about 75° C. to about 220° C. In another embodiment the temperature ranges from about 100° C. to about 200° C. In yet another embodiment the temperature ranges from about 140° C. to about 175° C. The temperature is in certain embodiments a key parameter in determining the particle size distribution of the product metal salt of the hydroxy-substituted aromatic compound, and avoiding salt accumulation on the walls of the drying vessel. Without being bound by any particular theory, it is proposed that the reason that temperature affects the particle size distribution and adhesion to vessel walls is because temperature affects the stability of various hydrates of the metal salt of the hydroxy-substituted aromatic compound. These hydrates are believed to be "sticky" and therefore responsible for particle agglomeration. Typically, the temperature at which the water-immiscible solvent into which the aqueous medium comprising the metal salt of hydroxy-substituted aromatic compound is sprayed, is greater than the boiling point of said aqueous medium under the prevailing pressure; preferably greater than the boiling point of water under the prevailing pressure.

The solution comprising the metal salt in the aqueous medium can be contacted with the water-immiscible solvent in various ways. In various embodiments the metal salt in the aqueous medium can be either fed in drop-wise into the water-immiscible solvent or it can be sprayed into the water-immiscible solvent. In one embodiment the metal salt in the aqueous medium is sprayed into the water-immiscible solvent. The sprayover velocity, the agitation intensity and the size of the aqueous droplets sprayed into the drying vessel are also important parameters in determining the dried salt particle size distribution and may also affect the tendency for salt to accumulate on the walls of the drying vessel.

In one embodiment, the drying vessel is equipped with a vapor handling system comprising a partial reflux condenser and a secondary condenser. The vapor stream that is formed during the contact of the aqueous medium comprising the metal salt of the hydroxy-substituted aromatic compound with the water-immiscible solvent, is introduced into the vapor handling system. The partial reflux condenser is typically maintained at a temperature below the boiling point of the water immiscible solvent under the prevailing conditions and above the boiling point of water under the prevailing conditions, which results in the separation of the vapor stream to provide a water-rich component and a water immiscible solvent-rich component. The water-immiscible solvent rich component may be condensed in the vapor handling system and returned back into the drying vessel. In one embodiment the partial condenser additionally serves as a means of capturing particles entrained out of the drying vessel (e.g. The partial reflux condenser functions as a 'knockout pot'). Typically the temperature of the partial reflux condenser ranges from about 100° C. to about 150° C. under atmospheric pressure which is high enough for water vapor to pass through and low enough for the water-immiscible solvent to condense within the partial reflux condenser. The water-rich component of the vapor stream, which emerges from the partial reflux condenser may be condensed in a secondary condenser. The water and any accompanying water-immiscible solvent may be separated, for example in a decanter, if desired. The water-immiscible solvent accompanying the water rich component may optionally be returned to the drying vessel. In one embodiment the water-rich component emerging from the partial reflux condenser comprises both water and the water-immiscible solvent, the water-immiscible solvent comprising less than about 50 percent by weight of the water-rich component emerging from the partial reflux condenser. In one embodiment the water-rich component emerging from the partial reflux condenser comprises both water and the water-immiscible solvent, the water-immiscible solvent comprising less than about 40 percent by weight of the water-rich component emerging from the partial reflux condenser. In another embodiment the water-rich component comprises between about 5 and about 98 percent by weight water. In yet another embodiment the water-rich component comprises between about 25 and about 98 percent by weight water. In still yet another embodiment the water-rich component comprises between about 45 and about 98 percent by weight water. Typically, the vapor stream introduced into the vapor handling system comprises between about 2 and about 40 percent by weight water. In one embodiment the vapor stream comprises between about 15 and about 35 percent by weight water. In another embodiment, for example in the preparation of 4,4'-biphenol disodium salt, the vapor stream comprises between about 2 and about 5 percent by weight water.

In one embodiment the water-immiscible solvent may be selected from compounds having formula

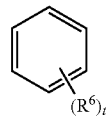

Formula III wherein $R^6$ is independently at each occurrence halogen, $C_1$-$C_6$ aliphatic radical, or $C_3$-$C_{12}$ aromatic radical; and "t" is an integer having a value 1-6. Suitable water-immiscible solvents may be selected from the group consisting of toluene, xylene, phenetole, anisole, veratrole, diphenylsulfone, chlorobenzene, bromobenzene, ortho-dichlorobenzene, meta-dichlorobenzene, para-dichlorobenzene, 1,3,5-trichlorobenzene, and 1,2,4-trichlorobenzene. In various embodiments suitable water-immiscible solvents in the present context are those which have a boiling point at atmospheric pressure of greater than about 90° C., or greater than about 150° C., or greater than about 170° C. In some embodiments suitable solvents also have a specific gravity of about 0.75 to about 1.5. In some particular embodiments suitable water-immiscible solvents have a specific gravity of greater than about 1.25.

The contacting of the metal salt of the hydroxy-substituted aromatic compound in an aqueous medium with a water-immiscible solvent in the drying vessel, may be carried out under agitation. The agitation can be maintained either for the entire time period required for drying or for a portion of the entire time period required for drying. In one particular embodiment said vessel comprises a stirred tank with at least one stirring shaft agitator. The degree of agitation is typically such as not to favor formation of salt cake in or on any part of the vessel or agitator which may be difficult to remove. In various embodiments the vessel comprises baffles beneath the surface of said water-immiscible solvent. At least two baffles may be present. In one embodiment greater than two baffles are present and in other embodiments between two and four baffles may be present. The design of the baffles is such that build-up of salt is not facilitated. In one particular embodiment the baffles are substantially vertical and are attached to the sides of the vessel, optionally starting at the tangent line from a curved surface at the bottom of the vessel should said vessel possess a curved bottom. Any baffle is attached to the side of the vessel at only 1, 2, or 3 or more spots on the baffle so that there is at least a partial gap between any baffle and the side of the vessel such that salt may pass through said gap and not collect to a significant extent against any baffle.

The drying vessel containing water-immiscible solvent may be fitted with equipment comprising at least one pipe and at least one spray nozzle for introduction of the aqueous medium comprising the metal salt of the hydroxy-substituted aromatic compound into said vessel. In one embodiment at least one pipe fitted with at least one spray nozzle conveys the aqueous medium comprising the metal salt of the hydroxy-substituted aromatic compound from the vessel in which the metal salt was prepared into the drying vessel containing water-immiscible solvent. One, two, three, four or more spray nozzles may be employed for introduction of the aqueous medium comprising the metal salt of the hydroxy-substituted aromatic compound into the drying vessel. In some embodiments 1 to 10 or 2 to 4 spray nozzles for introduction of aqueous medium comprising metal salt of hydroxy-substituted aromatic compound are employed. In one embodiment said spray nozzle or nozzles may project into the drying vessel from the top of the drying vessel. In another embodiment said spray nozzle or nozzles may be mounted flush with the top of the drying vessel to help prevent caking of salt. The spray of the aqueous medium comprising the metal salt of the hydroxy-substituted aromatic compound is directed to the surface of the water-immiscible solvent within the vessel, and preferably away from any agitator shaft and the sides of the vessel. The distance between any spray nozzle and the surface of the water-miscible solvent level may be any convenient distance to provide for spraying of the aqueous medium comprising the metal salt of the hydroxy-substituted aromatic compound into the vessel and formation of the vapor stream described above, with efficient use of the vessel space. In some embodiments a spray nozzle is at a distance of between about 0.15 to 3.0 meters or between about 0.3 to 2.5 meters or between about 0.3 to 1.5 meters above the suface of the water-immiscible solvent. Any dead space cavities in the vessel may be heated externally or flushed with dry/hot solvent to prevent any accumulation of water or metal salt cake therein. In one embodiment the vessel sides and top are traced with heating elements to provide external heating. In other embodiments provision may be made for contacting the top of the vessel and any dead spaces with hot water-immiscible solvent by spraying water-immiscible solvent therein. The water-immiscible solvent may comprise fresh solvent or solvent returned from condensate which was originally distilled from the vessel along with aqueous medium, or both fresh and returned solvent. Said spraying of water-immiscible solvent may be performed with equipment comprising at least one pipe and at least one spray nozzle for introduction of water-immiscible solvent. One, two, three, four or more spray nozzles may be employed for introduction of water-immiscible solvent into said vessel. In some embodiments 1 to 10 or 2 to 4 spray nozzles for introduction of water-immiscible solvent are employed. In one embodiment said spray nozzle or nozzles for introduction of water-immiscible solvent may project into the drying vessel from the top of the vessel. In another embodiment said spray nozzle or nozzles for introduction of water-immiscible solvent may be mounted flush with the top of the vessel to help prevent caking of salt. Water-immiscible solvent may be sprayed into the vessel as desired and in one embodiment is sprayed into the vessel simultaneously with spraying of aqueous medium comprising metal salt of hydroxy-substituted aromatic compound through separate spray nozzles.

The rate of introduction of the aqueous medium comprising the metal salt of a hydroxy-substituted aromatic compound into the vessel containing the water-immiscible solvent depends upon a number of factors, including, but not limited to, vessel size, temperature of the water-immiscible solvent, and amount of heating capability, and may be determined by one skilled in the art without undue experimentation. In some embodiments, if the rate of introduction is too high, then the temperature of the water-immiscible solvent may fall and the metal salt of hydroxy-substituted aromatic compound may tend to cake. In other embodiments, if the rate of introduction is too low, then process economics are less favorable. In general, the rate of introduction of aqueous medium comprising metal salt of hydroxy-substituted aromatic compound into the drying vessel containing water-immiscible solvent is as fast as possible to promote rapid formation of vapor stream without excessive caking of the salt. In particular embodiments the aqueous medium comprising the metal salt of a hydroxy-substituted aromatic compound is introduced into the vessel in such a manner that said medium does not impact the walls of the vessel or any stirrer shaft.

Heat may be provided to the water-immiscible solvent using any convenient method. In some embodiments heat is provided to the water-immiscible solvent by circulating said solvent through a heat exchanger. In a particular embodiment the heat exchanger is a tube-shell heat exchanger. In another particular embodiment the heat exchanger is a spiral heat exchanger or a self-cleaning reboiler. The rate of flow of the water-immiscible solvent-salt mixture through the heat exchanger is such that turbulent flow is achieved to prevent fouling of the heat exchanger by solid salt. The rate of flow depends upon a number of factors, including, but not limited to, the concentration of salt therein and the temperature, and may be determined without undue experimentation by one skilled in the art.

In one embodiment the drying vessel containing the water-immiscible solvent into which the aqueous medium comprising the metal salt of a hydroxy-substituted aromatic compound is introduced, may be under a positive pressure so that the temperature of water-immiscible solvent may be maintained above its normal boiling point at atmospheric pressure. In one embodiment the drying vessel may be maintained at a pressure ranging from about 0 psig to about 100 psig. In another the embodiment the pressure ranges from about 0 psig to about 50 psig. In yet another embodiment the pressure ranges from about 0 psig to about 25 psig. (0 psig refers to atmospheric pressure) In another embodiment the vessel holding the water-immiscible solvent into which the aqueous medium comprising metal salt of hydroxy-substituted aromatic compound is introduced may be maintained at sub-atmospheric pressure. Operating under sub-atmospheric pressure tends to lower the distillation temperature of the mixture for formation of vapor stream, and may help limit decomposition of the metal salt of hydroxy-substituted aromatic compound, which may occur at least to some extent at elevated temperatures depending upon the identity of the salt.

During the formation and removal of the vapor stream from the drying vessel any water-immiscible solvent exiting the vessel may optionally be replaced by adding additional water-immiscible solvent to the drying vessel. In one embodiment additional water-immiscible solvent is added to the drying vessel simultaneously with the vapor stream formation to keep the total volume of water-immiscible solvent substantially the same. As aqueous medium comprising water and optionally the water-miscible organic co-solvent are evaporated from the vessel some precipitated salt may be entrained in the distillate. In various embodiments entrained salt may be recovered using any known means. In a particular embodiment entrained salt may be removed from the vapor stream by a directing a spray of water-immiscible solvent into a vent through which the vapor stream with entrained salt passes upon exiting the vessel. The spray of water-immiscible solvent may be introduced at an angle to the flow of vapor stream that is convenient for removing at least a portion of entrained salt. In one particular embodiment at least one spray of water-immiscible solvent is introduced at an angle to the flow of vapor stream such that entrained salt is substantially removed, wherein "substantially removed" as described herein means that at least about 80% of the entrained salt is removed from the vapor stream. In various other embodiments at least about 85%, or at least about 90% of the entrained salt is removed, based on the weight of salt originally entrained. The entrained salt in the water-immiscible solvent may then be passed back to the drying vessel.

In one embodiment the slurry comprising the metal salt of a hydroxy-substituted aromatic compound in the water-immiscible solvent, may be obtained at a solids level in the water-immiscible solvent of between about 5 weight % to about 35 weight %. In another embodiment the solids level in the water-immiscible solvent is between about 10 weight % and about 30 weight %. In yet another embodiment the metal salt of hydroxy-substituted aromatic compound, may be obtained at a solids level in the water-immiscible solvent of between about 20 weight % and about 30 weight %. The weight percent of solids in the water-immiscible solvent is based on the total weight of the contents left behind in the drying vessel.

Before, during or after transfer to another vessel, or before use in any subsequent process such as in a polymerization reaction, the slurry comprising the metal salt of a hydroxy-substituted aromatic compound in a water-immiscible solvent may optionally be subjected to at least one drying step to remove any residual water. Said drying step may include, but is not limited to, combination with additional water-immiscible solvent and distillation, optionally at reduced pressure, or distillation of water-immiscible solvent from the mixture comprising water-immiscible solvent and metal salt, optionally with concomitant addition of dry water-immiscible solvent at approximately the same rate so as to keep the solvent amount roughly constant. Dry water-immiscible solvent in the context of the present process means solvent with less than about 100 parts per million (hereinafter referred to as ppm) water. In one embodiment at least one drying step takes place in the drying vessel in which the metal salt of a hydroxy-substituted aromatic compound was prepared. In other embodiments the slurry of the salt of the hydroxy-substituted aromatic compound in the water-immiscible solvent may be transferred from said vessel to at least one other vessel for an additional drying step. In one embodiment the amount of water remaining in the salt-containing water-immiscible solvent after one or more drying steps is less than about 100 ppm. In another embodiment the amount of water is less than about 60 ppm and in yet another embodiment the amount of water is less than about 40 ppm with respect to the weight of the dry salt present. The amount of water in the salt-containing water-immiscible solvent may be determined using known methods. In some embodiments the amount of water in the salt-containing water-immiscible solvent may be determined indirectly by measuring the water content of the vapor stream resulting from the contact of the aqueous medium comprising metal salt of hydroxy-substituted aromatic compound with the water-immiscible solvent in the drying vessel. The sprayover step (b) and drying may take place in one drying vessel, or at least one drying step may take place in a vessel different from the vessel used for the step (b) of sprayover.

If desired, the salt product may be separated from the water-immiscible solvent using any known method. In particular embodiments separation may be effected by filtration, or centrifugation, or like methods. Remaining traces of water-immiscible solvent in the salt may be removed, if desired, by methods such as vacuum drying, air drying or similar operation. It is, however, often convenient to employ the salt in a slurry form in the water-immiscible solvent without isolation of the salt. For example, the salt may be employed in slurry form in a subsequent reaction in which said salt is a reactant. In some embodiments the salt in water-immiscible solvent may be held in the vessel containing water-immiscible solvent into which the salt in aqueous medium was introduced or in a separate vessel, optionally at a lower temperature (for example, at about 120° C. to about 150° C.), and then transferred to a separate vessel for subsequent reaction.

For certain applications it may be particularly desirable that the product metal salt of the hydroxyl-substituted aromatic compound possess a certain particle size distribution. In some embodiments the metal salt has an average particle size below about 100 microns, as determined by laser diffraction using, for example, a Lasentec Particle Size Analyzer. In one embodiment the percentage of particles with diameter greater than about 200 nm is less than about 30% based on the total particles. In another embodiment the percentage of particles with greater that about 200 nm is less than about 25%. In yet another embodiment the percentage of particles greater that about 200 nm is less than about 20% based on the total particles. In another embodiment the percentage of particles with diameter greater than about 500 nm is less than about 5%. In yet another embodiment the percentage of particles with diameter greater than about 500 nm, is less than about 2% and in yet another embodiment the percentage of particles with diameter greater than about 500 nm is less than about 1% of the total particles. In one particular embodiment the percentage of particles with diameter greater than about 200 nm is less than about 25%, and the percentage of particles with diameter greater than about 500 nm is less than about 1% of the total particles.

In one embodiment the desired particle size range may be achieved either before, during or after transfer from the drying vessel containing water-immiscible solvent into which the metal salt in aqueous medium is introduced, to another vessel, such as a polymerization vessel, or following isolation of metal salt, by subjecting metal salt to at least one particle size reduction step. In a particular embodiment the metal salt may be subjected to at least one particle size reduction step in the presence of the water-immiscible solvent. Said particle size reduction step may employ commercially available equipment, including, but not limited to, one or more centrifugal pumps, grinders, drop-down blenders, particle size reduction homogenizers, and delumpers. Particle size reduction equipment may also comprise at least one homogenizer available from Silverson Machines, Inc., East Longmeadow, Mass.

The process for making metal salt described herein may be performed in batch mode, continuous mode or semi-continuous mode. The metal salt of hydroxy-substituted aromatic compound may be used in one or more subsequent reactions to form materials incorporating structural units derived from the hydroxy-substituted aromatic compound. In a particular embodiment a slurry of the metal salt in water-immiscible solvent may be used in a reaction to form a monomer for use in condensation polymerization. In another embodiment a slurry of metal salt in water-immiscible solvent may be used directly as a monomer in condensation polymerization. In yet another particular embodiment a slurry of metal salt of hydroxy-substituted aromatic compound in water-immiscible solvent may be used directly as a monomer in the preparation of polyethers such as, but not limited to, polyetherimides, polyethersulfones, polyetherimidesulfones, polyetherketones, polyetheretherketones, and the like. In an illustrative example the bis(sodium) salt of a dihydroxy-substituted aromatic compound may be used as a monomer to form a polyetherimide through reaction with at least one bis(N-(substituted phthalimido))aromatic compound. Suitable substituents on said bis(N-(substituted phthalimido)) aromatic compounds include any that can be displaced in a polymerization reaction with the metal salt of a hydroxy-substituted aromatic compound. In particular embodiments suitable substituents include, but are not limited to, nitro, halogen, chloro and bromo. Said polymerization reaction involving the displacement of reactive substituents may be performed in the presence of catalysts known to catalyze said reaction including, but not limited to, at least one hexa-substituted guanidinium salt, such as hexaethylguanidinium chloride. Said polymerization reaction may be performed in at least one solvent of low polarity, usually a solvent substantially lower in polarity than that of the dipolar aprotic solvents previously employed for the preparation of aromatic polyethers. In various embodiments said solvent has a boiling point above about 150° C. in order to facilitate the displacement reaction which typically requires temperatures in the range of between about 125° C. and about 250° C. Suitable solvents of this type include, but are not limited to, ortho-dichlorobenzene, para-dichlorobenzene, dichlorotoluene, 1,2,4-trichlorobenzene, diphenyl sulfone, phenetole, anisole, veratrole and mixtures thereof. Often said polymerization reaction is performed under conditions such that less than about 50 parts per million water is present with respect to dry weight of hydroxy-substituted aromatic compound salt.

Some embodiments of the invention may be better understood with reference to an illustrative example. In an embodiment of the invention a vessel (sometimes referred to herein as a drying vessel) is a tank comprising at least one agitator; at least one pressure indicator, at least one temperature indicator, solvent introduction lines and solvent return lines optionally comprising spray nozzles, inert gas connections, at least one spray nozzle to spray in metal salt of hydroxy-substituted aromatic compound in aqueous medium, an overheads line leading to a partial reflux condenser cooled with coolant that is supplied at a temperature about 5 degrees F. above the boiling point of water at the pressure of operation (preferably about 5 psig), said partial reflux condenser venting to a total condenser that is cooled with chilled water (preferably about 40-60 degrees F.), a back-pressure control valve in the overheads line, an accumulator downstream of the total condenser to receive and decant water, if water is present, from water-immiscible solvent, a pump-around loop leading out of and back into the drying vessel, said loop comprising a heat exchanger and a pump in the loop. Additional temperature and pressure indicators may be located at appropriate points. Typically the vessel also comprises subsurface baffles to reduce fouling by precipitated salt. Also an optional device or piece of equipment for reducing the particle size of the salt product may be present. If desired, the said particle size reduction device can be placed in the pump-around loop or can simply grind the salt product from the vessel as it is transferred to another vessel, such as to a polymerization reaction vessel. Alternatively, the said particle size reduction device (such as a drop-down blender) can be employed in the vessel itself.

EXAMPLES

The following examples are set forth to provide those of ordinary skill in the art with a detailed description of how the methods claimed herein are evaluated, and are not intended to limit the scope of what the inventors regard as their invention. Unless indicated otherwise, parts are by weight, temperature is in ° C.

Biphenol used for these experiments was obtained from Honshu Chemical Co.

Example 1

This Example Describes the Preparation of Aqueous Biphenol Disodium Salt

In a 3 liter Morton flask equipped with a water-cooled condenser, nitrogen bubbler, and a Teflon® blade impeller was added 4.4'-biphenol and aqueous sodium hydroxide to provide a aqueous salt solution. The flask was heated to and maintained at 85° C. The water-cooled condenser was maintained at 15° C. Both the salt solution preparation vessel and the drying vessel (into which the salt solution was added) were operated under atmospheric pressure. The details of the biphenol salt formulation are shown in Table I.

The aqueous salt solution was transferred at 99° C. into the drying vessel using a pump (This process is referred to as "sprayover"). The details of the sprayover conditions are given in Table 2. The drying vessel was a 3 liter Morton flask equipped with an electrically heated mantle, a Teflon paddle and a 316SS stir shaft. In Examples 1-3 the salt solution was dripped into the drying vessel, which initially contained 1900 gm orthodichlorobenzene (oDCB). In Example 4, the solution was introduced into the drying vessel via a subsurface dip tube. At the end of the sprayover, the drying vessel temperature was raised to 180° C. to completely dry the slurry. The flask headspace was continuously purged with a slow bleed of nitrogen (5-10 standard cc/min). Above the flask was mounted a partial reflux condenser cooled with a coolant circulated through temperature-controlled bath. The temperature of the coolant was maintained at 91-115° C. The vapors from the partial reflux condenser were directed to a second condenser through an insulated line. The second condenser was cooled with water from a bath maintained at 5° C. The temperature of the vapors leaving the first condenser was recorded. The weight fraction of oDCB in the condensate from the second condenser was measured. The oDCB in the flask was periodically sampled and analyzed for water content by Karl-Fischer titration. No fresh oDCB was added during sprayover. Table 3 shows the particle size distribution and the fraction biphenol salt that adhered to the vessel walls for examples 1-5. The quantity of material adhering to the vessel walls was determined by first dissolving the salt in methanol, evaporating the methanol, and then weighing the solid.

Examples 1-2 show that at lower drying vessel temperatures (150-160° C.) a significant fraction of the biphenol salt adheres to the drying vessel walls and the salt product has a large average particle size. Examples 3-4 show that at a drying vessel temperature of 170° C., there is no particle adhesion to the vessel walls and the particle size is significantly smaller. Further, Examples 3-4 show that the sprayover feed may be introduced either above or below the surface of the oDCB in the drying vessel.

Example 5

This Example Demonstrates the Aqueous Process on a Pilot Scale

In this example the aqueous biphenol salt was fed from a temperature-controlled pressure tank at controlled flow rate into the drying vessel containing oDCB. The aqueous salt solution was introduced above the surface of the agitated oDCB via a drip nozzle. The feed solution was not atomized. No oDCB was added to the drying vessel during sprayover. The drying vessel comprised a glass-lined steel vessel equipped with an oil jacket, a three-blade retreating anchor impeller, a reflux condenser, and a small nitrogen purge. The vapors leaving the partial reflux condenser were condensed in a total condenser. Both the condensers were cooled with water (20° C.); and the temperature of the vapor leaving the partial reflux condenser was monitored. All condensate from the total condenser was collected and characterized for the weight fraction oDCB. After the sprayover was complete, the temperature of the drying vessel was elevated to 180° C. and the reflux discontinued by stopping the coolant flow to the partial reflux condenser. After no further water was visually detected in the condensate, the drying vessel was allowed to cool. The product was then vacuum filtered. The wet cake was then reslurried in fresh oDCB for particle size analysis via a Lasentec PT-100 particle size analyzer.

TABLE 1

Biphenol Salt Solution Formulations in water

| Example | Weight percent[a] of biphenol disodium salt | Biphenol (grams) | Weight percent sodium hydroxide | Sodium hydroxide solution (grams) | Water (grams) |
|---|---|---|---|---|---|
| 1 to 4, CE-4 | 23.4 | 200 | 49.84 | 171 | 684.0 |
| 5 | 23.4 | 1837 | 50.773 | 1554.3 | 6312.0 |

[a]based on the weight of aqueous solution.

TABLE 2

Sprayover Conditions with Partial Reflux Condenser

| Example | oDCB Temp, ° C. | Feed Rate (gm/min) | Overhead Temp, ° C. | weight fraction oDCB in overheads[d] | Water in oDCB (ppm) |
|---|---|---|---|---|---|
| 1 | 150 | 2.1 | 98 | 0.45 | 250 |
| 2 | 160 | 2.1 | 98 | 0.48 | 190 |
| 3[b] | 170 | 2.1 | 101 | 0.46 | 50 |
| 4 | 170 | 2.3 | 107 | 0.52 | 105 |
| 5 | 170 | 83.4[c] | 146 | 0.78 | — |

[b]subsurface feed (1/8" 316SS open tube)
[c]average feed rate (initial rate was 250 gm/min for 5 minutes)
[d]also referred to as water-rich component

TABLE 3

BP Salt Particle Size Distribution

| Example | Solvent | oDCB Temp ° C. | Volume-Average Diameter, microns | weight fraction biphenol disodium salt on vessel walls | weight fraction >1 mm |
|---|---|---|---|---|---|
| 1 | Water | 150 | 326 | 0.846 | 0.089 |
| 2 | Water | 160 | 324 | 0.073 | 0.007 |
| 3[d] | Water | 170 | 130 | 0 | 0 |
| 4 | Water | 170 | 127 | 0 | 0 |
| 5 | Water | 170 | 226 | 0 | 0 |

[d]subsurface feed (1/8" 316SS open tube)

Comparative Examples 1-2

These Examples Demonstrate the Methanol Process for the Preparation of Biphenol Disodium Salt and Drying In comparative examples 1-2 the same apparatus as described above was used for the preparation of aqueous salt solution of biphenol sodium salt, however in this case methanol was used instead of water. The methanol-biphenol sodium salt solution was maintained at room temperature for comparative example 1 and at 50° C. for comparative example 2. Each solution was sprayed into 1700 gm oDCB at 150° C. The oDCB was agitated at 450 rpm with a Teflon paddle. The reaction flask in this case was fitted with a distillation head and all the condensate from this distillation head was collected. No oDCB was added to the drying vessel during sprayover. These lab tests showed no accumulation of disodium salt on the drying vessel walls. The average particle size depends on the weight fraction BPNa$_2$ in the methanol feed. These examples demonstrate that the lab apparatus is capable of producing acceptable metal salt. The reactant composition for preparing the aqueous salt solution, the sprayover condition in the drying vessel and the results are tabulated in Table 4, Table 5, and Table 6 respectively.

Comparative Example 3

Demonstrates the Methanol Process on a Pilot Scale

In this example, room temperature methanol-BPNa$_2$ salt solution was sprayed over into 116 kg oDCB maintained at 150° C. The resulting particle size distribution (161 micron volume-average median diameter) was suitable for subsequent uses of the material (drying, polymerization to polyetherimide). Although this process yields an excellent particle size distribution and operates at a relatively low sprayover temperature, it has the disadvantage that it employs a large quantity of volatile, flammable solvent. The reactant composition for preparing the aqueous salt solution, the spray over condition in the drying vessel and the results are tabulated in Table 4, Table 5 and Table 6 respectively.

TABLE 4

Biphenol sodium salt formulation in methanol

| Comparative Example | Weight percent[e] of biphenol disodium salt | Biphenol (grams) | Weight percent of sodium hydroxide | Sodium hydroxide solution (grams) | Methanol (grams) |
|---|---|---|---|---|---|
| 1 | 15 | 200 | 49.84 | 171 | 1273.8 |
| 2 | 25 | 200 | 49.84 | 171 | 617.0 |
| 3 | 17.6 | 4250 | 50.65 | 3602.6 | 21990 |

[e]based on the weight of sprayover solvent employed.

TABLE 5

Sprayover Conditions with Distillation Head (no partial condenser)

| Comparative Example | oDCB Temp ° C. | Feed Rate (gm/min) | weight fraction oDCB in overheads[a] | Water in oDCB (ppm) |
|---|---|---|---|---|
| 1 | 150 | 5.7 | 0.42 | — |
| 2 | 150 | 3.3 | 0.60 | 117 |
| 3 | 150 | 112 | 0.69 | — |

[a]also referred to as vapor stream

TABLE 6

| | | | BP Salt Particle Size Distribution | | |
|---|---|---|---|---|---|
| Comparative Example | Solvent | oDCB Temp °C. | Volume-Average Diameter, microns | weight fraction of biphenol disodium salt on Vessel walls | weight fraction >1 mm |
| CE-1 | Methanol | 150 | 152 | 0 | 0 |
| CE-2 | Methanol | 150 | 274 | 0 | 0 |
| CE-3 | Methanol | 150 | 161 | 0 | 0 |

Comparative Example 4

Sprayover at 170° C. with Short Path Condenser

The 3-liter sprayover vessel described in examples 1-4 was fitted with a short path condenser, which was cooled with 10° C. coolant. No vapors were returned to the sprayover vessel; all vapors were distilled, condensed, and collected outside of the sprayover vessel. This vessel was charged with 1900 gm oDCB and heated to 170° C. When aqueous solution of biphenol disodium salt was introduced (composition given in Table I), the oDCB vaporization rate was so rapid that it was not feasible to maintain an inventory of oDCB in the vessel.

The invention has been described in detail with particular reference to preferred embodiments thereof, but it will be understood by those skilled in the art that variations and modifications can be effected within the spirit and scope of the invention.

What is claimed is:

1. A method for preparing a metal salt of a hydroxy-substituted aromatic compound, said method comprising steps (a)-(d):
   (a) contacting in an aqueous medium at least one hydroxy-substituted aromatic compound with a base comprising a metal cation to provide a mixture comprising water and a metal salt of said hydroxy-substituted aromatic compound;
   (b) contacting the mixture formed in step (a) with a substantially water-immiscible solvent at a temperature greater than the boiling point of water at the prevailing pressure to provide a slurry comprising the metal salt of the hydroxy-substituted aromatic compound and the water immiscible solvent, and a vapor stream comprising the substantially water-immiscible solvent and water;
   (c) introducing the vapor stream into a vapor handling system comprising a partial reflux condenser; and
   (d) separating the vapor stream to provide a water-rich component and a water immiscible solvent-rich component.

2. The method of claim 1, wherein the contacting in step (b) is achieved by spraying the mixture formed in step (a) into the substantially water-immiscible solvent.

3. The method of claim 1, wherein the hydroxy-substituted aromatic compound is selected from the group consisting of monohydroxy-substituted aromatic compounds; dihydroxy-substituted aromatic compounds; trihydroxy-substituted aromatic compounds; tetrahydroxy-substituted aromatic compounds, and mixtures thereof.

4. The method of claim 1 wherein the hydroxy-substituted aromatic compound is at least one dihydroxy-substituted aromatic compound having formula I

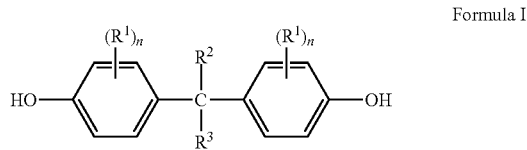

Formula I wherein $R^1$ is independently at each occurrence a halogen, a $C_1$-$C_{30}$ aliphatic radical, a $C_3$-$C_{30}$ cycloaliphatic radical, or a $C_3$-$C_{30}$ aromatic radical, $R^2$ and $R^3$ are independently hydrogen, a $C_1$-$C_{30}$ aliphatic radical, a $C_3$-$C_{30}$ cycloaliphatic radical, a $C_3$-$C_{30}$ aromatic radical, or $R^2$ and $R^3$ together form a $C_3$-$C_{20}$ cycloaliphatic radical, and "n" is an integer having a value 0 to 4.

5. The method of claim 1 wherein the hydroxy-substituted aromatic compound is at least one dihydroxy-substituted aromatic compound having formula II

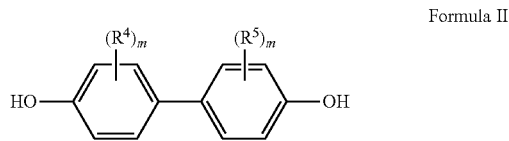

Formula II wherein $R^4$ and $R^5$ are independently at each occurrence halogen, a $C_1$-$C_{30}$ aliphatic radical, a $C_3$-$C_{30}$ cycloaliphatic radical, or a $C_3$-$C_{30}$ aromatic radical, and "m" is an integer having a value 0 to 4.

6. The method of claim 1 wherein the hydroxy-substituted aromatic compound is selected from the group consisting of 2,2-bis(4-hydroxyphenyl)propane (bisphenol-A) and 4,4'-dihydroxybiphenyl.

7. The method of claim 1 wherein said vapor stream comprises vapors of the water-immiscible solvent in an amount corresponding to about 3 kg per kg water vapor to about 50 kg per kg water vapor.

8. The method of claim 1, wherein water-rich component comprises less than about 50 percent by weight of the water-immiscible solvent.

9. The method of claim 8, wherein water-rich component comprises less than about 30 percent by weight of the water-immiscible solvent.

10. The method of claim 1 wherein the metal cation is sodium.

11. The method of claim 1 wherein the base and the hydroxy-substituted aromatic compound are present in amounts corresponding to a molar ratio of base to hydroxy-substituted aromatic compound which deviates from ideal stoichiometry by no more than 0.4 mole %.

12. The method of claim 1 wherein the water-immiscible solvent comprises at least one solvent having formula III

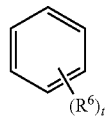

Formula III wherein $R^6$ is independently at each occurrence a halogen, a $C_1$-$C_6$ aliphatic radical, or a $C_3$-$C_{12}$ aromatic radical; and "t" is an integer having a value 1-6.

13. The method of claim 12 wherein the water-immiscible solvent is selected from the group consisting of toluene, xylene, phenetole, anisole, veratrole, diphenylsulfone, chlorobenzene, bromobenzene, ortho-dichlorobenzene, 1,3-dichlorobenzene, 1,4-dichlorobenzene, 1,3,5-trichlorobenzene, and 1,2,4-trichlorobenzene.

14. The method of claim 1 wherein the water-immiscible solvent is selected from the group consisting of toluene, ortho-dichlorobenzene, and mixtures thereof.

15. The method of claim 1 wherein the contacting in step (b) is carried out at a temperature in a range from about 75° C. to about 220° C.

16. The method of claim 1 further comprising filtering said slurry comprising the metal salt of the hydroxy-substituted aromatic compound and the water immiscible solvent to provide a solid alkali metal salt of the hydroxy-substituted aromatic compound.

17. The method of claim 1 wherein the metal salt comprises less than 25% of particles with a diameter of greater than about 200 microns.

18. A method for preparing an alkali metal salt of a hydroxy-substituted aromatic compound of formula IV, said method comprising steps (a)-(d):

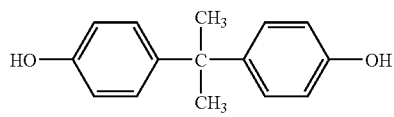

Formula IV (a) contacting in an aqueous medium the hydroxy-substituted aromatic compound of formula IV with a base comprising an alkali metal cation to provide a mixture comprising water and an alkali metal salt of said hydroxy-substituted aromatic compound of formula IV;
(b) contacting the mixture formed in step (a) with a substantially water-immiscible solvent at a temperature greater than the boiling point of water at the prevailing pressure to provide a slurry comprising the alkali metal salt of the hydroxy-substituted aromatic compound of formula IV and the water immiscible solvent, and a vapor stream comprising the substantially water-immiscible solvent and water;
(c) introducing the vapor stream into a vapor handling system comprising a partial reflux condenser; and
(d) separating the vapor stream to provide a water-rich component and a water immiscible solvent-rich component.

19. A method for preparing an alkali metal salt of a hydroxy-substituted aromatic compound of formula V, said method comprising steps (a)-(d):

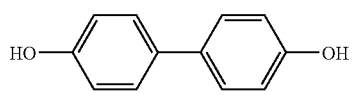

Formula V (a) contacting in an aqueous medium the hydroxy-substituted aromatic compound of formula V with a base comprising an alkali metal cation to provide a mixture comprising water and an alkali metal salt of said hydroxy-substituted aromatic compound of formula V;
(b) contacting the mixture formed in step (a) with a substantially water-immiscible solvent at a temperature greater than the boiling point of water at the prevailing pressure to provide a slurry comprising the alkali metal salt of the hydroxy-substituted aromatic compound of formula V and the water immiscible solvent, and a vapor stream comprising the substantially water-immiscible solvent and water;
(c) introducing the vapor stream into a vapor handling system comprising a partial reflux condenser; and
(d) separating the vapor stream to provide a water-rich component and a water immiscible solvent-rich component.

20. A method for preparing a metal salt of hydroxyl-substituted aromatic compound, said method comprising steps (a)-(d):
(a) contacting in an aqueous medium at least one hydroxyl-substituted aromatic compound with a base comprising a metal cation to provide a mixture comprising water and a metal salt of said hydroxyl-substituted aromatic compound;
(b) contacting the mixture formed in step (a) with a substantially water-immiscible solvent at a temperature greater than the boiling point of water at the prevailing pressure to provide a slurry comprising the metal salt of the hydroxyl-substituted aromatic compound and the water immiscible solvent, and a vapor stream comprising the substantially water-immiscible solvent and water;
(c) introducing the vapor steam into a vapor handling system comprising a partial reflux condenser; and
(d) separating the vapor stream to provide a water-rich component and a water immiscible solvent-rich component;
wherein the process is practiced without a co-solvent.

* * * * *